United States Patent [19]

Lash et al.

[11] 3,934,347

[45] Jan. 27, 1976

[54] DENTAL PROSTHETIC STRUCTURE AND METHOD

[75] Inventors: Harvey Lash; Morris Kibrick, both of Palo Alto; Shirl S. Fox, Menlo Park, all of Calif.

[73] Assignee: Lash Oral Implants, Palo Alto, Calif.

[22] Filed: Jan. 14, 1975

[21] Appl. No.: 540,949

[52] U.S. Cl. .............................. 32/10 A; 128/92 C
[51] Int. Cl.² ........................................ A61C 13/00
[58] Field of Search ...... 32/10 A; 128/92 C; 3/1.91, 3/1.5

[56] References Cited
UNITED STATES PATENTS

| | | | |
|---|---|---|---|
| 3,689,942 | 9/1972 | Rapp | 3/1.5 |
| 3,827,145 | 8/1974 | Richards | 32/10 A |

FOREIGN PATENTS OR APPLICATIONS

| | | | |
|---|---|---|---|
| 1,306,027 | 2/1973 | United Kingdom | 3/1.91 |

Primary Examiner—Louis G. Mancene
Assistant Examiner—Jack Q. Lever
Attorney, Agent, or Firm—Stephen P. Fox

[57] ABSTRACT

A dental implant includes a porous ceramic cup or ring filled with silicone rubber which supports an artificial tooth or other prosthetic device such as a denture. The jawbone grows into the porous ceramic to hold the implant firmly in place. The silicone rubber cushions the jawbone from shock caused by multidirectional masticatory forces. A fibrous matting is partially embedded into the upper periphery of the silicone rubber that extends from the ceramic cup or ring. Gingival tissue becomes attached to the matting to form a seal that precludes bacteria from invading and infecting the implant area. In another embodiment, the implant includes a metal sleeve completely filled with and surrounded by silicone rubber. Fibrous matting is partially embedded into the surface of the silicone rubber. Both the jawbone and the gingival tissue adhere to the matting to hold the implant firmly in place and to prevent bacterial invasion.

16 Claims, 8 Drawing Figures

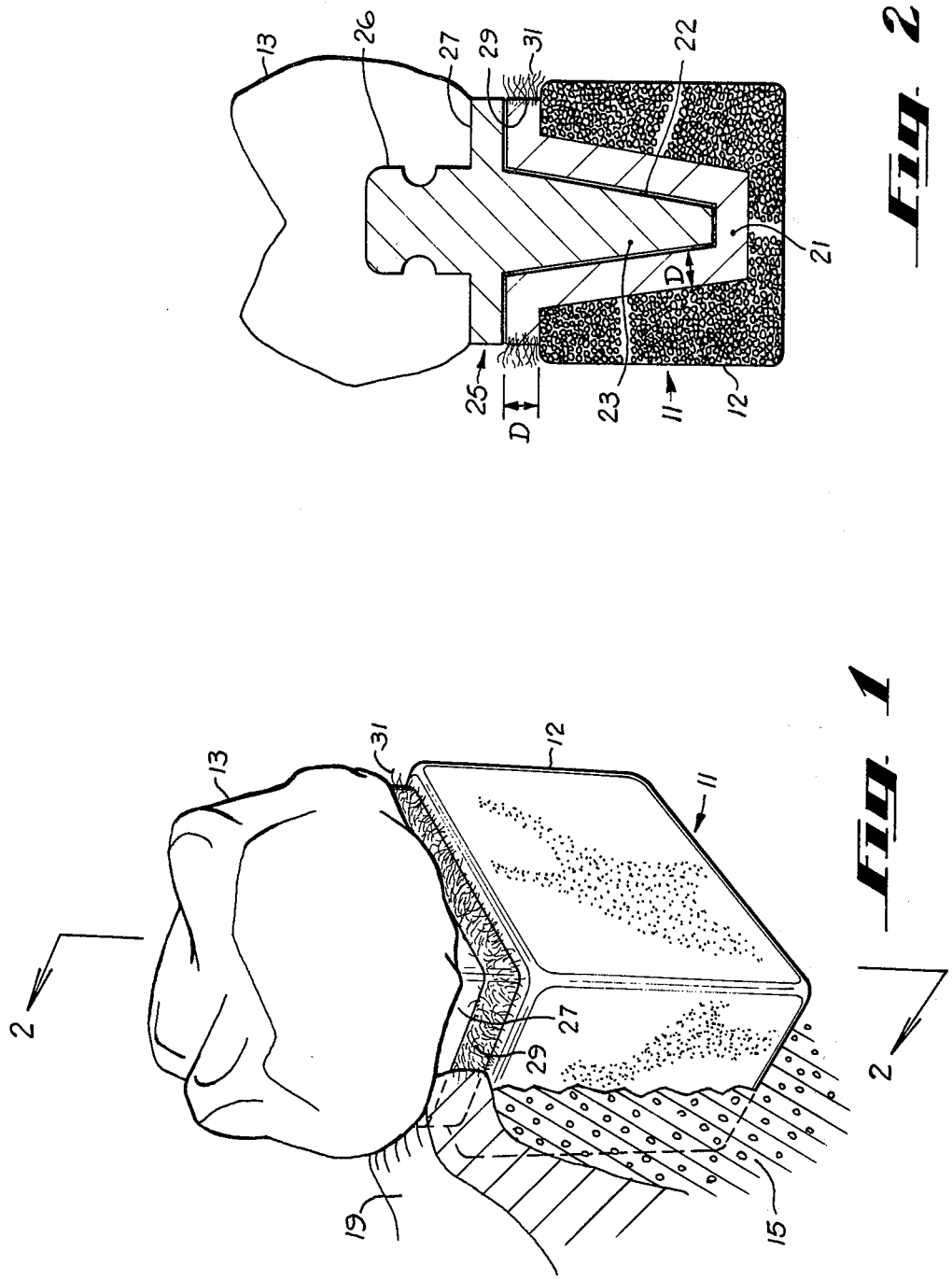

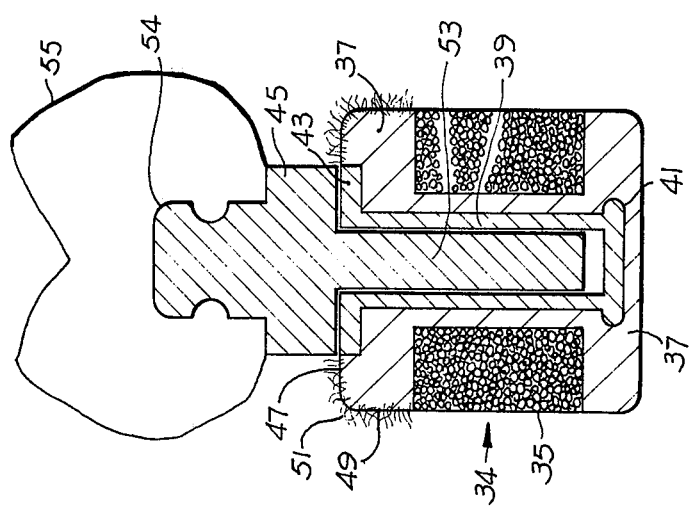
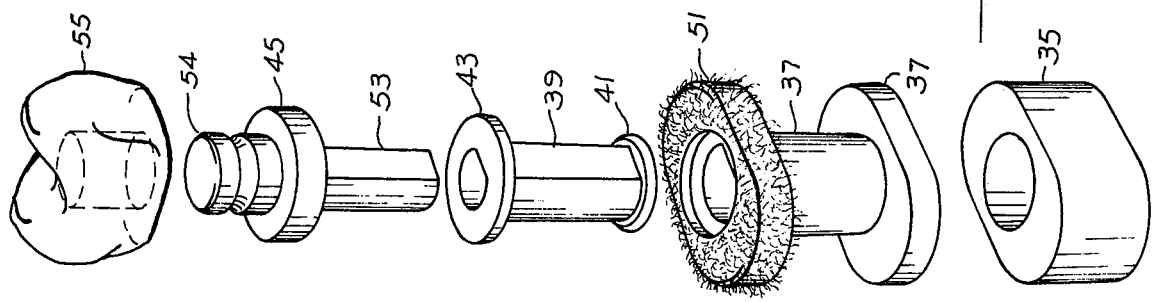

DENTAL PROSTHETIC STRUCTURE AND METHOD

BACKGROUND OF THE INVENTION

The present invention relates to a dental prosthetic structure including an implant for insertion into a patient's jawbone.

Artificial implants for replacing missing teeth are known in the art. A common problem encountered is that of adequately securing the tooth or denture to the patient's existing jawbone. In an attempt to overcome this problem, a variety of devices and techniques have been proposed. Typically, the artificial tooth is attached to an implant that is configured with large protrusions. When the implant is inserted into the jawbone, the bone forms around the protrusions, thereby creating a mechanical interlock. The resulting construction is initially firmly held by the jawbone; however, in time the implant is unable to withstand masticatory forces. These forces are transmitted by the implant to the supporting jawbone and, as a result, the implant is loosened. At first, a small pocket develops between the implant and the surface of the gingival tissue. Bacteria invade this pocket and infect the surrounding area. As this condition progresses, the infected pocket becomes larger and extends downward to the interface of the implant and the supporting bone. Ultimately, the implant is rejected by the jaw.

Attempts have been made to cushion the implant from the adverse effects of masticatory forces by providing a mechanical spring or a thin sheet of resilient material within the prosthetic structure. However, such devices have failed to adequately protect the implant, and in time it loosens in the jaw and is rejected.

SUMMARY OF THE INVENTION

The present invention comprises a prosthetic implant device that becomes firmly attached to the jawbone and adequately absorbs the shock of multidirectional masticatory forces, thereby reducing substantially the risk of rejection of the implant by the jaw. According to one illustrated embodiment of the invention, the implant comprises a porous ceramic cup or ring that is filled with a resilient material such as silicone rubber. The silicone rubber suspends a metal receptacle which receives a mating pin that is part of an artificial tooth assembly. The implant is first inserted into a cavity in the jawbone of a patient and the jaw is allowed to heal. In time, the bone grows into the interstices of the porous ceramic so that the implant becomes an integral part of the jaw. Thereafter, the artificial tooth is secured in place by cementing the pin of the tooth into the socket of the implant. The artificial tooth in effect "floats" in its silicone rubber support and dissipates multidirectional forces produced on the tooth during mastication. In use, the implant simulates the shock absorption characteristics of the periodontal membrane, i.e., the resilient support in the implant yields in response to mastication forces to cushion the jawbone.

Extending from the upper periphery of the silicone rubber support is a synthetic fibrous material such as Dacron matting. With the implant in place in the jaw, the matting is exposed contiguously to the gingiva. As the gingiva grows and surrounds the implant, it becomes attached to the matting. The resulting bond precludes bacteria from invading the area surrounding the implant, thereby substantially reducing the risk of pocket formation, infection and consequent rejection of the implant.

Another illustrated embodiment of the present invention comprises an implant in which a metal ring is filled with, and externally surrounded by, silicone rubber or other resilient material. A receptacle is suspended in the filler within the ring to provide a floating support for the mating tooth assembly, as described above. A feature of this embodiment is that Dacron or other fibrous material, either woven or matting, extends from the entire lateral surface of the resilient material. Thus, with the implant in place in the jaw, the fibrous material is contiguous to the surrounding jawbone as well as the gingiva. As the bone and gingiva grow around the implant, they both become firmly attached to the matting. The interface between the jawbone and implant is composed entirely of the resilient silicone rubber and fibrous material, thereby enhancing the shock-absorbing characteristics of the implant and reducing the transmission of masticatory forces to the jawbone.

BRIEF DESCRIPTION OF THE DRAWINGS

FIG. 1 is a perspective view of one embodiment of the implant and artificial tooth assembly of the present invention situated in the jawbone.

FIG. 2 is a cross-sectional view taken along the line 2—2 of FIG. 1.

FIG. 3 is a perspective exploded view of a second embodiment of the implant and artificial tooth assembly of the present invention.

FIG. 4 is a cross-sectional view of the implant of FIG. 3 in assembled form.

DESCRIPTION OF THE PREFERRED EMBODIMENTS

Figure 6:
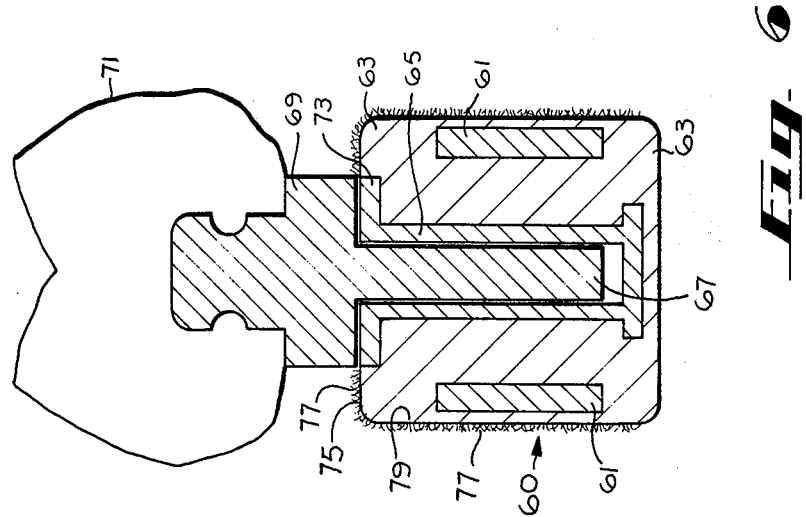
FIG. 6 is a cross-sectional view taken along the line 6—6 of FIG. 5.

Referring now to FIGS. 1 and 2, there are shown perspective and cross-sectional views of a dental prosthetic structure including an implant portion 11 and a crown portion 13. FIG. 2 illustrates the implant portion 11 situated in the bone tissue of the alveolar process 15 of a patient's jaw. As described hereinafter, the implant is placed in a socket resulting in the alveolar process after extraction of a tooth or in a bony socket prepared in an edentulous area. The gingival tissue 19 surrounds the socket at the upper portion of implant 11. Crown 13 extends above the gingiva and comprises an artificial tooth prepared according to the surrounding dentition, as described hereinafter.

Implant portion 11 includes a cup-shaped structure 12 having a rectangular or oval cross section. Cup 12 is formed of a porous ceramic material such as alumina. Alternatively, cup 12 may be formed of metal externally covered with a porous composition of tetrofluoroethylene and carbon such as Proplast (available from Smith Kline Corporation, Philadelphia, Pa.). The ceramic cup 12 is filled with a resilient material 21, such as silicone rubber. The resilient material 21 completely surrounds and securely suspends a receptacle 22. A pin portion 23 of a tooth support 25 is secured in receptacle 22 with dental cement. The receptacle 22 and tooth mounting means 25 are fabricated from metal such as Vitallium, Tantallum, noble metals, or surgical stainless steel. The upper portion of the tooth mount 25 defines a post 26 to which the crown 13 is attached. Crown 13 is typically formed of acrylic or porcelain, and extends above the gingival tissue 19, as shown.

According to one method of fabricating the implant structure 11, cup 12 is placed in a surrounding mold and receptacle 22 is positioned therein. A mixture of silicone rubber is prepared in liquid form and air bubbles are removed from it under vacuum. The silicone rubber is of medical grade, such as Silastic (available from Dow-Corning Corporation, Midland, Mich.). The silicone rubber is poured into the mold which holds the ceramic cup 12 and allowed to cure at room temperature. Alternatively, silicone putty may be cut into bits, then firmly inserted between the cup 12 and receptacle 22 and heat cured.

The silicone rubber resilient material 21 extends above the ceramic cup 12 to hold the flange 27 of tooth support 25 in spaced-apart relation with the cup 12. The spacing D between tooth support 25 and cup 12 is typically 1.5 millimeters. The peripheral surface area 29 of resilient material 21 interfaces with the gingival tissue 19. A fibrous matting or woven material 31 extends from the peripheral surface 29 of the resilient material 21 so as to be exposed to the gingival tissue 19. Matting 31 is formed of synthetic fibers such as Dacron. The matting or woven material 31 is either embedded into the resilient material 21 or glued onto the material using a suitable medical adhesive.

When the prosthetic structure is situated in a socket of the jawbone, the bone tissue 15 grows into the interstices of the porous cup 12. In effect, cup 12 becomes an integral part of the jaw. The resilient material 21 completely surrounds the receptacle 22 that holds the pin 23 of tooth support 25. Thus, tooth support 25 is suspended in spaced-apart relation with cup 12. With this arrangement, tooth support 25 and the crown 13 attached thereto in effect float in the implant 11. The implant dissipates multidirectional forces produced on crown 13 during mastication. More specifically, the implant simulates the shock-absorption characteristics of the periodontal membrane that exists between a normal living tooth is extracted, or is non-existent in edentulous areas, it is no longer present to surround the implant. Instead, the resilient material 21 in the implant yields in response to masticatory forces applied in any direction to cushion the jawbone in much the same manner as the periodontal membrane cushions a living tooth. This cushioning effect substantially reduces the possibility that masticatory forces will dislodge the implant in the jawbone and cause pockets to form at the interface between the implant and the surrounding bone tissue. As described above, if such pockets form, they are susceptible to invasion by bacteria which infect the area surrounding the implant and ultimately cause the implant to be rejected by the jaw.

The fibrous material 31 interfaces with the gingival tissue 19 and becomes attached to the gingival tissue as it grows to surround the implant structure. Consequently, the gingival tissue becomes firmly secured to the implant just below the crown 13, and forms a seal with the resilient material 21 at the peripheral surface area 29. This seal precludes bacteria from invading the implant socket.

After the jaw has healed around the implant, there is provided a dental prosthetic structure that is substantially integral with the jawbone, that cushions the jawbone from masticatory forces applied in any direction, and that seals the implant socket from the invasion of bacteria. The implant is illustrated with a single artificial tooth. However, it will be understood that the implant may also be used to support a denture including a plurality of artificial teeth. In this case, post 26 of tooth support 25 is suitably configured for securing it to an anchor point on the denture.

Another embodiment of the dental prosthetic structure is illustrated in FIGS. 3 and 4. As shown, an implant 34 comprises an oval-shaped porous ceramic ring 35. Silicone rubber or other resilient material 37 is formed in and around the ring 35 in a manner similar to that described above with respect to FIG. 2. Briefly, according to one method of forming the implant, ring 35 is placed in a cup-like mold that permits the silicone rubber to be formed above and below the ring 35 and in the same peripheral shape as the ring. A metal receptacle 39 is suspended internally of ring 35 in spaced-apart relation therewith during formation of the silicone rubber. Receptacle 39 has a lower flange portion 41 which locks it firmly in place when surrounded by the silicone rubber. Receptacle 39 also has an upper flanged portion 43 which interfaces with a metal tooth support 45. The external dimensions of tooth mounting means 45 and flange 43 are smaller than the external dimensions of the ceramic ring 35 and the silicone rubber molded about the upper portion thereof. Thus, the silicone rubber is exposed on the top surface portion 47 of the implant as well as the lateral surface portion 49. Fibrous matting or woven material 51 is embedded into or glued onto the silicone rubber 37 at both surfaces 47 and 49. The fibrous material extends from the implant to interface with the gingival tissue when the implant is in place in a socket in the jaw. As described above, as the implant heals in place, bone tissue of the alveolar process grows into the interstices of the porous ceramic ring 35, and the gingival tissue becomes attached to the fibrous material 51 to seal the implant socket area from bacteria. After the jaw has healed, the pin 53 of artificial tooth support 45 is cemented into receptacle 39. Affixed to a post 54 of tooth support 45 is a crown 55 prepared according to the surrounding dentition.

Figure 5:
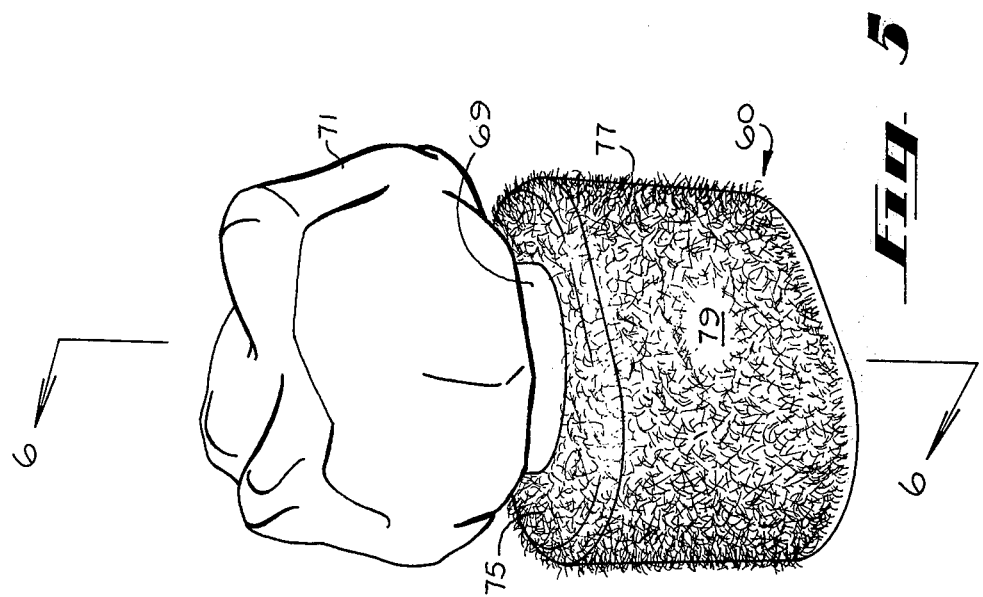
FIG. 5 is a perspective view of a third embodiment of the implant and artificial tooth assembly of the present invention.

FIGS. 5 and 6 illustrate another embodiment of the dental prosthetic structure according to the present invention. An implant 60 comprises an oval-shaped metal ring 61, made of Vitallium or Tantallum, for example. Ring 61 is filled with and completely surrounded by resilient material 63, which is silicone rubber as described above. Internally of supporting ring 61, there is suspended a metal receptacle 65, also formed of Vitallium, Tantallum or the like. Receptacle 65 is disposed in spaced-apart relation with the internal walls of ring 61, so as to float in the resilient material 63, thereby to provide absorption of shock due to multidirectional masticatory forces. Cemented in receptacle 65 is a mating pin 67 which is part of a tooth support member 69, the upper portion of which mounts a crown 71. Receptacle 65, mating pin 67, tooth support 69 and crown 71 are configured substantially the same as described above with reference to FIGS. 2 and 4.

The external dimensions of the upper flange 73 of receptacle 65 and the interfacing portion of the tooth support 69 are less than the external dimensions of the implant, so that the top surface 75 of the silicone rubber 63 surrounding the tooth support is exposed. Fibrous matting or woven material 77 is attached to and extends from the silicone rubber on this top surface 75. Also, the fibrous material 77 is attached to and extends from the silicone rubber 63 over the entire lateral surface 79 of the implant. When the implant is situated in a socket of the jawbone, the top surface 75 and the upper portion of lateral surface 79 of the implant are disposed contiguously to the gingival tissue, whereas the lower portion of lateral surface 79 interfaces with the bone tissue of the alveolar process. As the jaw heals with the implant in place, the gingival tissue attaches to the fibrous matting on the upper portion of the implant and the bone tissue attaches to the fibrous matting on the lower surface of the implant. The metal ring 61 provides internal rigidity for the implant, while both the bony tissue and gingival tissue of the jaw interface with the resilient silicone rubber material 63. The resilience of the silicone rubber within the implant and at the bone-implant interface cushions the jaw from multidirectional masticatory forces, thereby reducing shock on the jaw which might dislodge the implant and form pockets subject to infection. The attachment of the gingival tissue to the upper portion of the implant serves to seal the implant socket from bacterial invasion.

According to the method of installing the dental prosthetic structure in the mouth of a patient, a socket is prepared in the jaw in the area where a tooth has been extracted or in an edentulous region. The implant is inserted into this socket without the crown and associated metal support mounted thereon. The implant may have the configuration of any of the three embodiments described above, namely, implant 11 (FIGS. 1 and 2), implant 34 (FIGS. 3 and 4), or implant 60 (FIGS. 5 and 6). After the implant is placed in the prepared socket in the jaw, the gingival tissue is sutured over it and the jaw is permitted to heal for a period of about 6 to 8 weeks. During this time, the bony tissue of the alveolar process grows into the porous portion of the implant, or attaches to the fibrous material in the case of the embodiment of FIGS. 5 and 6. Also, during this time, the gingival tissue adheres to the fibrous material on the upper portion of the implant.

After the jaw has healed, the gingival tissue is removed to expose the metal receptacle which floats in the resilient material of the implant. Thereafter, the pin portion of the tooth support (e.g., pin 23 of support 25 in FIG. 2) is temporarily inserted into the metal receptacle. At this time, the upper post portion of the tooth support is exposed and does not have a crown or denture mounted on it.

Figure 7:
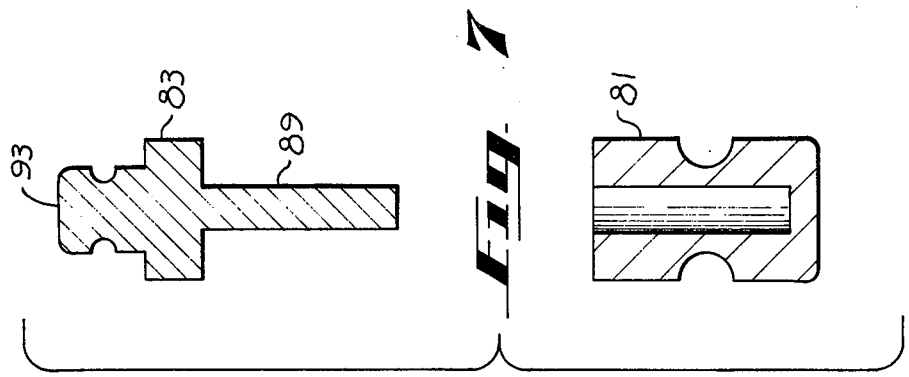
FIG. 7 is a perspective view of a pin and counter-die used in forming an artificial tooth in the manner shown in FIG. 8.
Figure 8:
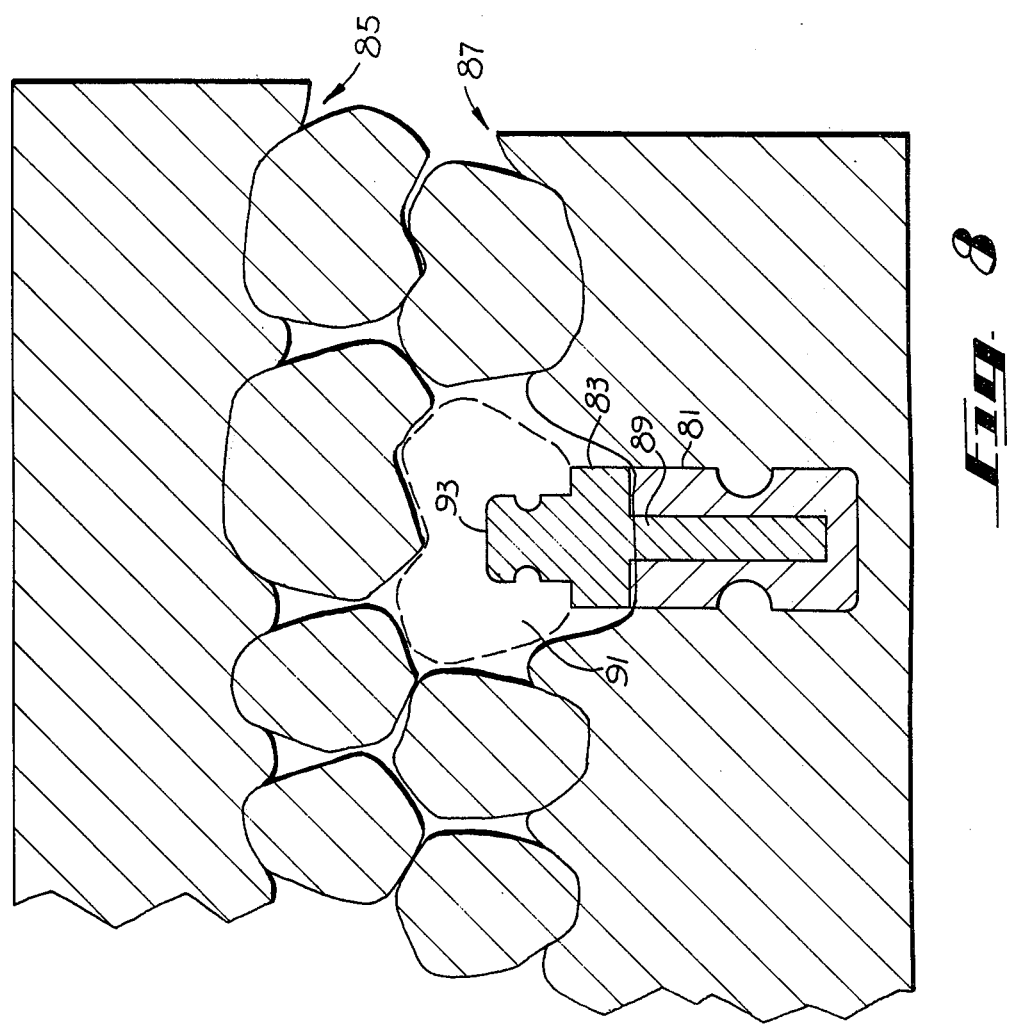
FIG. 8 is a cross-sectional view of dental casts illustrating the method in which an artifical tooth is formed for attachment to the implant.

An impression is made of the dental arch surrounding the implant and protruding post in conventional dental impression material such as hydrocolloid or synthetic rubber. The post of the tooth support becomes imbedded in the impression material, and the tooth support is withdrawn with the impression when it is removed from the dental arch. With the tooth support imbedded in the impression material, the pin thereof is exposed. An acrylic counter-die 81 of the configuration shown in FIG. 7 is placed over the exposed pin, represented by pin 83. Thereafter, as shown in FIG. 8, a cast or model 87 of the impression is made by investing the impression in plaster, which is then permitted to harden. Another cast 85 is made of the opposing dental arch. The acrylic counter-die 81 is set in the plaster mold of the teeth in the same spatial relationship with adjacent and opposing teeth that exists in the mouth of the patient. The pin 89 of tooth support 83 is inserted into the counter-die 81 and a crown 91 of acrylic or other suitable plastic or porcelain is constructed on the post 93 of the tooth support. Preferably, the crown is baked directly onto the post and then carved to fit against the adjacent and opposing teeth represented by the plaster mold thereof. The crown 91 and its associated tooth support 83 are then removed from the counter-die 81 and permanently cemented into the metal receptacle in the implant situated in the patient's mouth (e.g., receptacle 22 in FIG. 2).

By taking a dental impression of both dental arches with the tooth support in place in the implant, and thereafter making a mold of the dental arches containing the counter-die, the tooth support is positioned in the plaster mold of the dental arches in exactly the same spatial relationship to surrounding teeth as it is in the mouth of a patient. This permits the tooth support and the crown to be constructed as a single unit outside of the mouth using laboratory techniques which would be unsatisfactory if attempted within the mouth of a patient. For example, the process of baking the crown onto the tooth support could not be achieved without substantial discomfort to the patient and even then the fluid conditions inside the mouth of the patient would interfere with attempts to attach a crown to the post.

What is claimed is:

1. Apparatus comprising:
   a hollow ceramic member having a porous exterior surface for interfacing with bone tissue;
   mounting means for securing a dental prosthetic device; and
   means including a resilient material disposed in the interior portion of said hollow member for suspending said mounting means in spaced-apart relation with the interior surface of said hollow member, said suspending means being resilient to multidirectional masticatory forces applied to said mounting means.

2. The device of claim 1, wherein said resilient material is silicone rubber filling the hollow portion of said hollow member.

3. The device of claim 1, wherein said mounting means is a receptacle suspended in said resilient material.

4. The device of claim 3, further including an artificial tooth having a mounting pin secured in said receptacle.

5. The device of claim 1, wherein said hollow member is a porous ceramic cup.

6. The device of claim 1, wherein said hollow member is a porous ceramic ring.

7. The device of claim 1, wherein said hollow member has an external porous surface composed of tetrafluoroethylene and carbon fibers.

8. The device of claim 1, further including fibrous material secured to said resilient material and disposed adjacent to the periphery of said hollow member for interfacing with gingival tissue.

9. The device of claim 8, wherein said resilient material is silicone rubber and said fibrous material is partially embedded in said resilient material.

10. The device of claim 8, wherein said fibrous material is composed of synthetic fibers.

11. A method of preparing a dental prosthetic device to be secured to an implant in a patient's mouth, the method comprising the steps of:
- temporarily mounting a tooth support member on said implant;
- forming an impression of the teeth adjacent to and opposing said tooth support member in dental impression material;
- removing said impression from the patient's mouth, thereby to remove said tooth support member embedded in said impression material;
- placing a counter-die on the portion of said tooth support member exposed from said impression material;
- casting said impression, including said counter-die, in dental casting material to reproduce the implant mount and the adjacent and opposing teeth in said casting material in the same spatial relationship as in the patient's mouth.

12. The method of claim 11, further including the steps of:
- molding a crown of artificial tooth material onto said tooth support member supported on said counter-die, said crown being formed in cooperative relation with the adjacent and opposing teeth reproduced in said dental casting material;
- securing said crown to said tooth support member to form a unitary artificial tooth; and
- securing said unitary artificial tooth to said implant mount in the patient's mouth.

13. The method according to claim 12, wherein the step of securing said crown to said tooth support member to form a unitary artificial tooth is by baking said crown onto said tooth support member.

14. Apparatus comprising:
- a hollow member having a porous exterior surface for interfacing with bone tissue;
- mounting means for securing a dental prosthetic device;
- means disposed in the interior portion of said hollow member for suspending said mounting means, said suspending means being resilient to multidirectional masticatory forces applied to said mounting means; and
- fibrous material secured to said resilient material and disposed between said hollow member and said dental prosthetic device for interfacing with gingival tissue to permit formation of a seal with the gingival tissue, thereby to preclude invasion of bacteria into the area surrounding said hollow member.

15. The device of claim 14, wherein said resilient material is silicone rubber and said fibrous material is partially embedded in said resilient material.

16. The device of claim 14, wherein said fibrous material is composed of sythetic fibers.

* * * * *

UNITED STATES PATENT AND TRADEMARK OFFICE
CERTIFICATE OF CORRECTION

PATENT NO. : 3,934,347
DATED : January 27, 1976
INVENTOR(S) : Harvey Lash, Morris Kibrick and Shirl S. Fox It is certified that error appears in the above–identified patent and that said Letters Patent are hereby corrected as shown below:

Column 3, line 49, after "tooth", insert --and the bone tissue of the alveolar process. Since the periodontal membrane is destroyed when a tooth--.

Signed and Sealed this thirteenth Day of April 1976

[SEAL]

Attest:

RUTH C. MASON
Attesting Officer

C. MARSHALL DANN
Commissioner of Patents and Trademarks